US009808563B2

(12) United States Patent
Pirzada et al.

(10) Patent No.: US 9,808,563 B2
(45) Date of Patent: Nov. 7, 2017

(54) BREAST PUMP AND SYSTEM OR PROGRAM FOR PUMPING BREASTS

(71) Applicant: GENADYNE BIOTECHNOLOGIES, INC., Hicksville, NY (US)

(72) Inventors: Shahzad Saad Pirzada, Old Westbury, NY (US); Chien Ming Goh, Syosset, NY (US); Maria Elizabeth Lynch, Fort Lauderdale, FL (US)

(73) Assignee: GENADYNE BIOTECHNOLOGIES, INC., Hicksville, NY (US)

( * ) Notice: Subject to any disclaimer, the term of this patent is extended or adjusted under 35 U.S.C. 154(b) by 88 days.

(21) Appl. No.: 14/398,341

(22) PCT Filed: May 3, 2013

(86) PCT No.: PCT/US2013/039576
§ 371 (c)(1),
(2) Date: Oct. 31, 2014

(87) PCT Pub. No.: WO2013/166462
PCT Pub. Date: Nov. 7, 2013

(65) Prior Publication Data
US 2015/0112298 A1 Apr. 23, 2015

Related U.S. Application Data

(60) Provisional application No. 61/642,416, filed on May 3, 2012.

(51) Int. Cl.
*A61M 1/06* (2006.01)
(52) U.S. Cl.
CPC .............. *A61M 1/062* (2014.02); *A61M 1/06* (2013.01); *A61M 2205/123* (2013.01);
(Continued)

(58) Field of Classification Search
CPC ............ A61M 1/06; A61M 2205/3334; A61M 2205/3584; A61M 2205/50; A61M 2205/52
See application file for complete search history.

(56) References Cited

U.S. PATENT DOCUMENTS 7,835,230 B1 * 11/2010 Chang ................. G04G 15/006
368/109
8,801,658 B2 * 8/2014 Harari ................. A61B 5/1075
604/74

(Continued)

OTHER PUBLICATIONS

Preliminary Report on Patentability and Written Opinion of the International Searching Authority, dated Nov. 13, 2014.
(Continued)

*Primary Examiner* — Quynh-Nhu H Vu
(74) *Attorney, Agent, or Firm* — Collard & Roe, P.C.

(57) ABSTRACT

There is a breastfeeding device having a microprocessor having a memory embedded therein that can be pre-programmed to have a plurality of different sucking cycles interspersed with periodic pauses. These different cycles and pauses allow for an accurate modeling of a woman breastfeeding a child. In addition, this system and process can also result in a pre-programmable breastfeeding pump, which creates a preset time for initialization and a preset schedule of a series of events for breastfeeding over a period of time such as over a 24 hour or 30 hour period of time so that the user can automatically use the breast pump without having to use any of the keys on the keyboard of the device. In at least one embodiment, the device including any software which can be programmed thereon, is configured to mimic or model itself towards a suction pattern of a child.

8 Claims, 11 Drawing Sheets

(52) U.S. Cl.
CPC .............. *A61M 2205/3334* (2013.01); *A61M 2205/3584* (2013.01); *A61M 2205/50* (2013.01); *A61M 2205/52* (2013.01); *A61M 2205/75* (2013.01)

(56) References Cited

U.S. PATENT DOCUMENTS

| | | | |
|---|---|---|---|
| 9,162,016 B2 * | 10/2015 | Geddes | A61M 1/06 |
| 2004/0122358 A1 | 6/2004 | Kent et al. | |
| 2005/0228342 A1 | 10/2005 | Yuen | |
| 2007/0010760 A1 | 1/2007 | Rosenfeld | |
| 2007/0135761 A1 * | 6/2007 | Cheng | A61M 1/06 604/74 |
| 2008/0009815 A1 * | 1/2008 | Grabenkort | A61M 1/0031 604/346 |
| 2008/0045887 A1 * | 2/2008 | Larsson | A61M 1/06 604/74 |
| 2011/0004154 A1 * | 1/2011 | Van Schijndel | A61M 1/06 604/74 |
| 2011/0153365 A1 * | 6/2011 | Meier | G06F 19/322 705/3 |
| 2012/0004603 A1 | 1/2012 | Harari et al. | |

OTHER PUBLICATIONS

International Search Report of PCT/US2013/039576, dated Sep. 16, 2013.

\* cited by examiner

BREAST PUMP AND SYSTEM OR PROGRAM FOR PUMPING BREASTS

CROSS REFERENCE TO RELATED APPLICATIONS

This application is the National Stage of PCT/US2013/039576 filed on May 3, 2013, that claims priority under 35 U.S.C. 119e from provisional application Ser. No. 61/642,416 filed on May 3, 2012 the disclosure of which is hereby incorporated herein by reference in its entirety. The international application under PCT article 21(2) was published in English.

BACKGROUND OF THE INVENTION

The invention relates to a breast pump and a system for pumping breasts. This system is configured to perform a plurality of steps which are configured to pump breast milk or other fluids from a breast.

SUMMARY OF THE INVENTION

In at least one embodiment, there is a system and process that results in a breastfeeding device having a microprocessor having a memory embedded therein that can be pre-programmed to have a plurality of different sucking cycles interspersed with periodic pauses. These different cycles and pauses allow for an accurate modeling of a woman breastfeeding a child. In addition, this system and process can also result in a pre-programmable breastfeeding pump, which creates a preset time for initialization and a preset schedule of a series of events for breastfeeding over a period of time such as over a 24 hour or 30 hour period of time so that the user can automatically use the breast pump without having to use any of the keys on the keyboard of the device.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
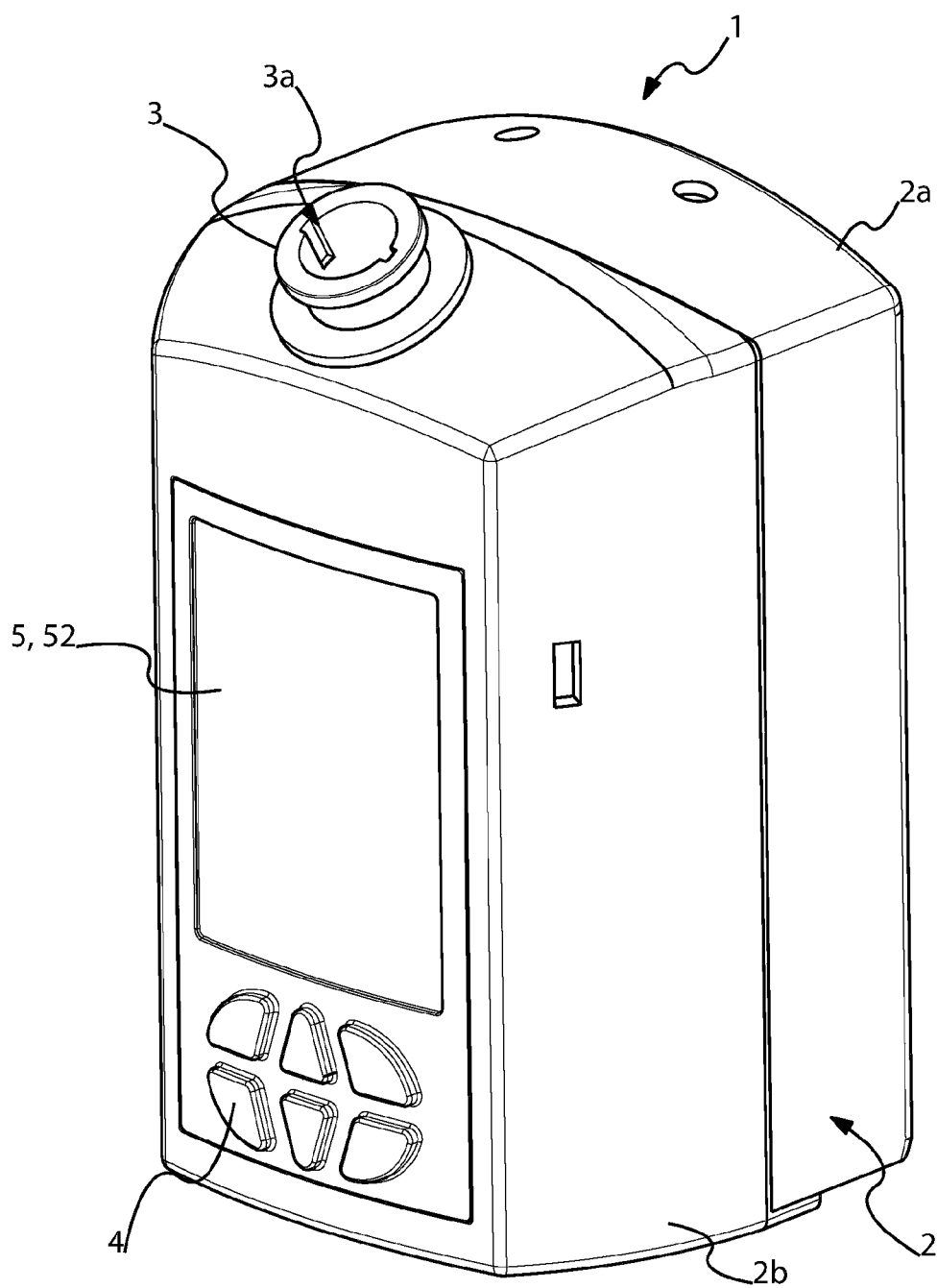
FIG. 1 is a perspective view of a pump.

Turning in detail to the drawings, FIG. 1 shows a perspective view of a pump which can be configured for any particular use, but in at least one embodiment is configured as a breast pump. This pump 1 includes a cover 2 including a back cover section 2a and a front cover section 2b. Back cover section 2a and front cover section 2b can be selectively separated from each other so that a user can (if necessary) have access to the internal components shown in greater detail in FIG. 3. There is an output/input port or opening 3 which is shown extending out from a top angled section of the housing. Port or opening 3 includes a cylindrical opening which can be made from any suitable material, and which has at least one slot 3a which is configured to allow for a connection of a tube therein to allow the tube to lock therein. This output/input port creates a selective push or suction pressure for creating a fluid pressure inside of a tube that is selectively coupled to port or opening 3.

A keypad 4 is shown coupled to housing 2, wherein keypad 4 includes a plurality of keys which allow a user to selectively scroll through a number of options.

A screen such as a LCD screen having a front cover 5 and an electronic screen component 52 is shown disposed in housing 2. Buttons 4 and screen 52 is also shown in greater detail in FIG. 3.

Figure 2:
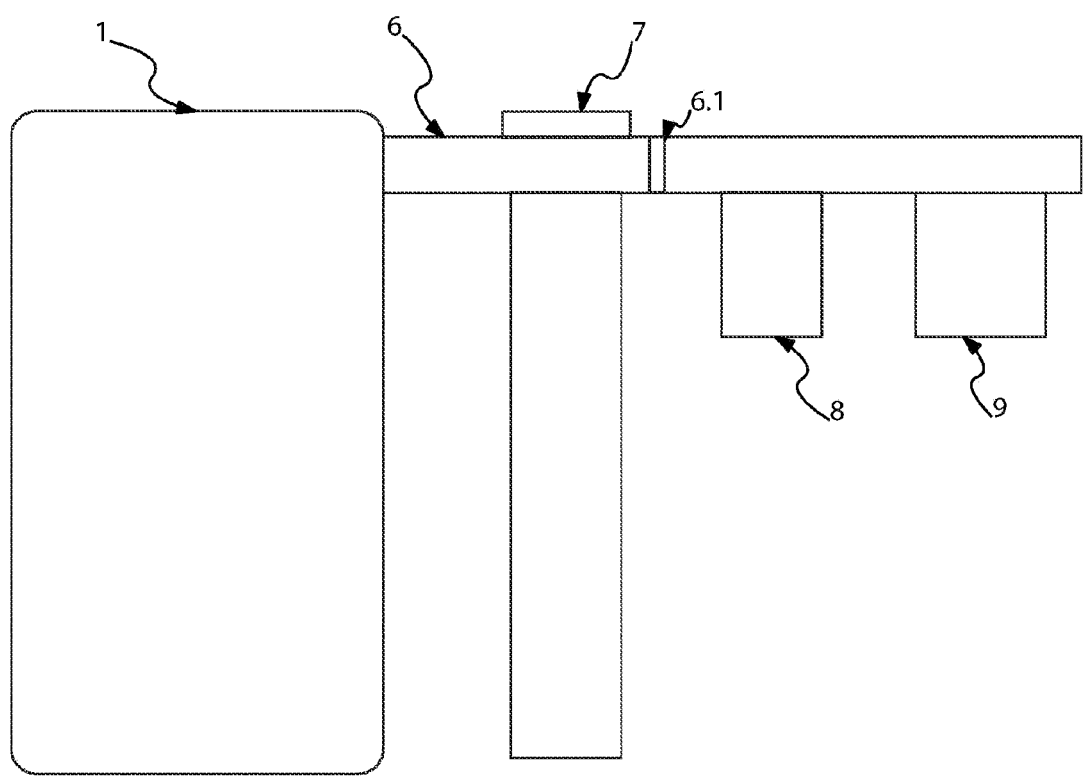
FIG. 2 is a side view of the pump and filter configuration.

FIG. 2 shows an optional configuration of fluid into the device wherein this optional configuration is configured to allow for the fluid flow through at least two filters 8 and 9 along line 6. Line 6 is coupled to receptacle 7 and is configured to allow fluid such as milk to flow through this line and into opening 3 shown in FIG. 1. Each of these filters 8 and 9 are selectively removable from the line, while the receptacle 7 is also removable such that receptacle 7 can serve as a reservoir for the fluid such as milk drawn from a woman's breast. A first filter 8 can be used for a first sized particulate matter, while a second filter 9 can be of a different size for different particulate matter. The provision of the two filters in line allows for more rapid flow of fluid by separating out different sized particles at different times.

Figure 3:
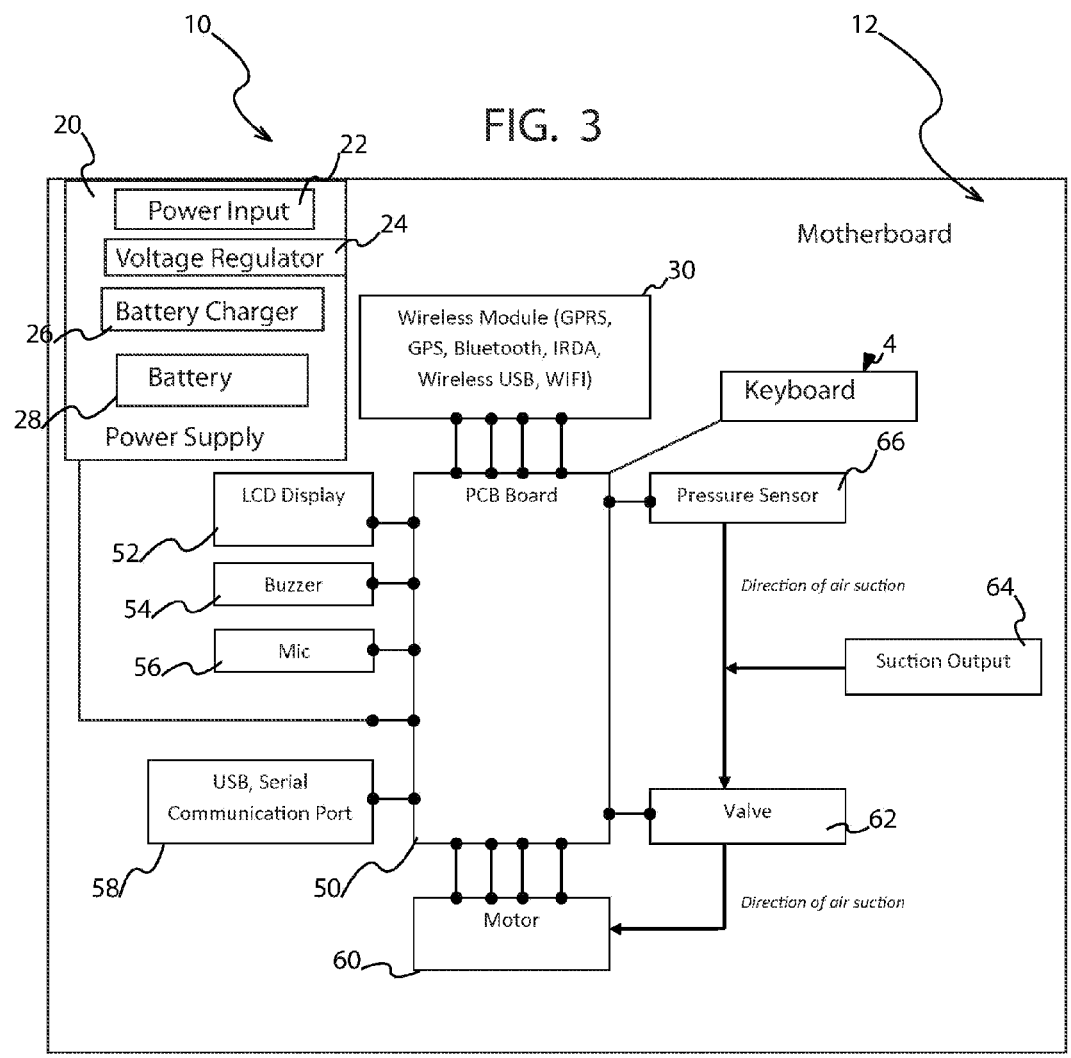
FIG. 3 is a schematic block diagram of electronic components that can be used for the pump shown in FIG. 1.

FIG. 3 shows a schematic block diagram for the electronic components that are housed inside of housing 2. These components 10 include a motherboard 12 which is configured to house and selectively electrically connect all of the components shown in FIG. 2. For example, there is a power supply 20 including a power input 22, a voltage regulator 24 which could be a multi voltage regulator such as a 3V voltage regulator or a 12 V voltage regulator. The output of this voltage regulator can feed into battery charger 26. Battery charger 26 can include at least one processor configured to control the charging of an associated battery 28. The output of battery charger 26 feeds in to battery 28. Battery 28 can be in the form of any suitable battery such as a nickel cadmium battery or a lithium ion battery. This power supply also can provide power to the system such as to the motherboard 12. This device or system can include a wireless module which can be in the form of any suitable wireless module 30. The wireless module can include any one of a GPRS telecommunications chip or assembly, a GPS (global positioning system) chip, bluetooth chip, infrared (IRDA), wireless (802.11 a, b, g, n etc).

A controller which can be in the form of a microcontroller 50 is coupled to motherboard 12 as well and receives power from power supply 20. This controller can be any suitable type of controller which can be in the form of a Atmel AT91SAM7SE256. This type of controller is an ARM7TDMI based High-performance 32-bit RISC Microcontroller with Thumb extensions, —256K Bytes Flash, 32K Bytes SRAM, clock up to 48 MHz, —USB 2.0 Full Speed, —88 I/O Pins, Memory Controller, Reset Controller, Clock Generator, Debug Unit, Power Management Controller, Advanced Interrupt Controller, Periodic Interval Timer, Windowed Watchdog, Real-time Clock, 11 Peripheral DMA Controller Channels, 3-channel 16-bit Timer/Counters, 4-channel PWM, Two USARTs, Synchronous Serial Controller, Serial Peripheral Controller, 2wire Interface, 8-channel 10-bit ADC, 4 High-current Drive I/O lines.

Figure 4:
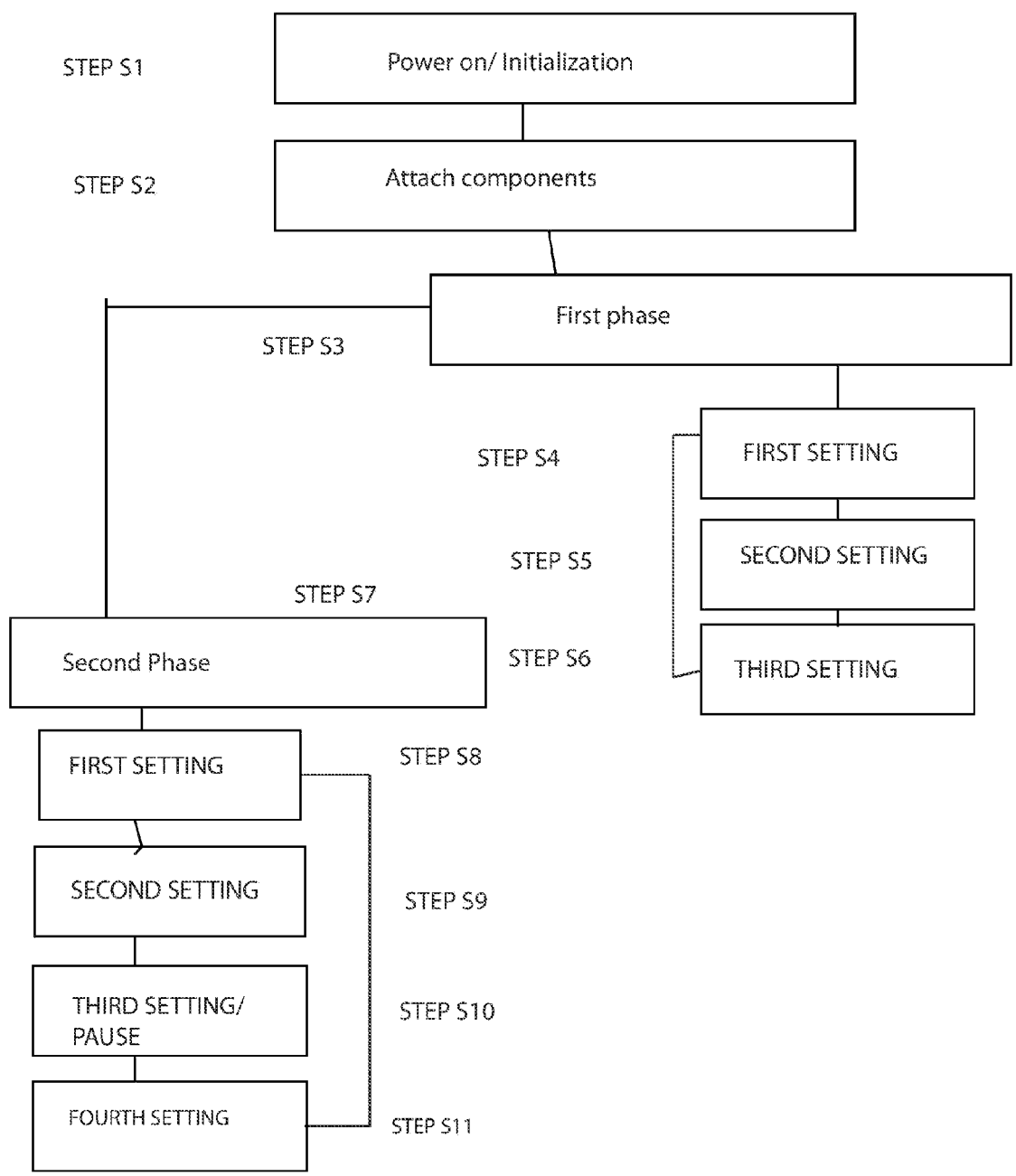
FIG. 4 is a flow chart for the pump in use.
Figure 6:
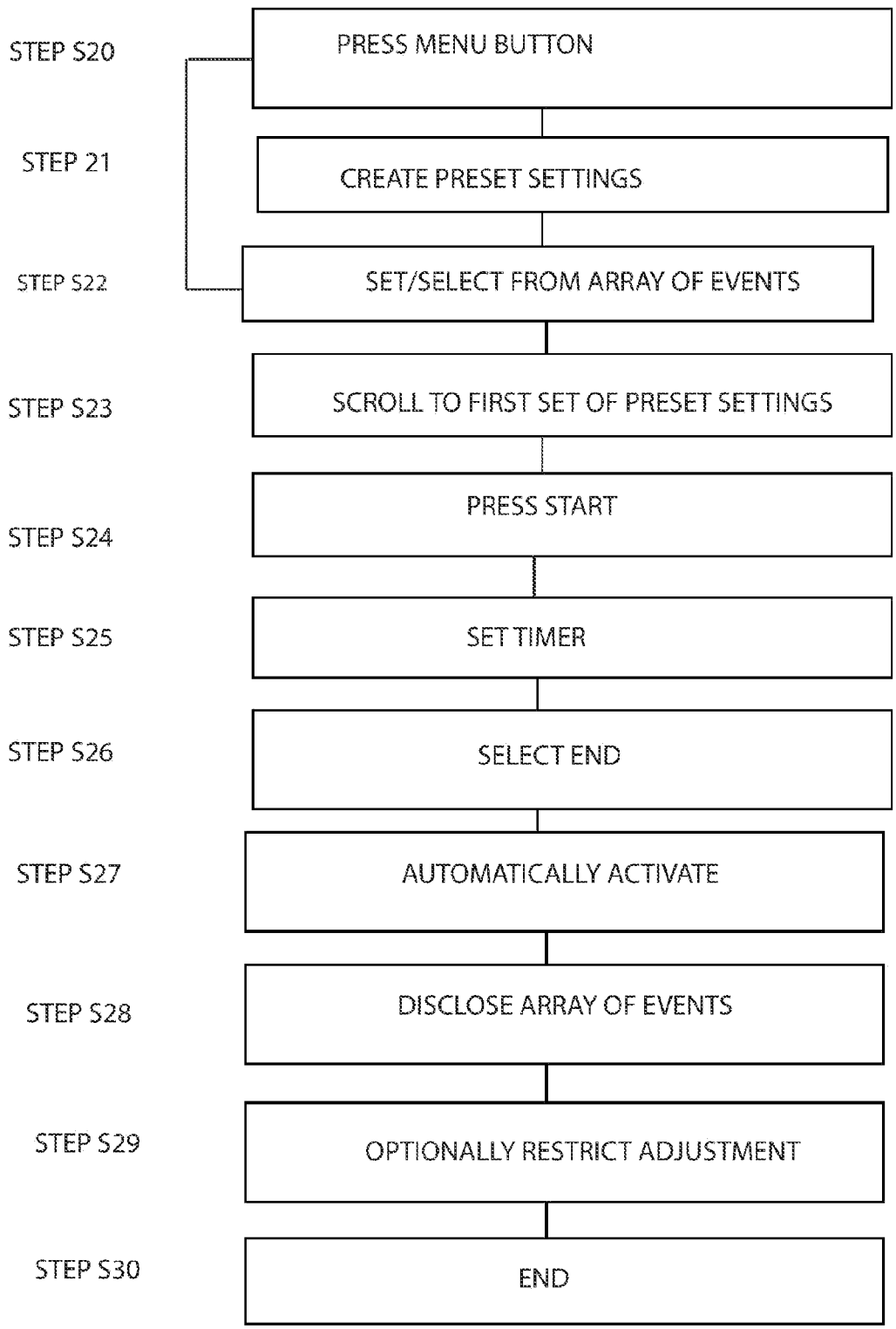
FIG. 6 is as flow chart for a preset timer setting for the pump.

This controller can be configured to perform a series of pre-programmed steps such as those shown in FIGS. 4 and 6. For example, controller can as indicated above include an onboard memory which stores this information including a program configured to perform the series of steps outlined in FIGS. 4 and 6 and then based upon input from the keyboard or based upon a timer prompt, start a series of steps shown in FIGS. 4 and 6.

Controller 50 is also coupled to, or in communication with a number of other components such as a LCD display 50, a buzzer or audio annunciator 54, a microphone 56, a USB or serial communication port 58. LCD display 52 is shown in greater detail in FIG. 1 and is configured to provide the user with the ability to view the status of the machine as well as allow the user to use the keypad to scroll through the different options on the machine. The buzzer 54 is configured as an audio annunciator so that when either an alarm goes off or when the device switches from one phase to another phase, such as from phase 1 to phase 2 as indicated in FIGS. 3 and 4 then this buzzer can announce this switch. There can also be a microphone 56 which is configured to read or receive audio statements from a user. A USB port can also be present. This USB port can be any suitable USB port such as a USB port having a USB filter such as a USBUF02W6 manufactured by ST microelectronics and a USB connector made by Hirose Connector.

In addition, coupled to the PCB or micro controller or microprocessor 50 is a motor 60 wherein motor 60 is configured as a pump which provides a blowing force out from valve or opening 3 or a suction pressure into opening 3. Motor 60 can be any suitable motor and is configured to provide this pneumatic pressure through valve 62, which is coupled to micro controller 50 and is configured to be controlled by micro controller 50. A suction output 64 is fluidly coupled to valve 62 and is configured to allow fluid such as air or other suitable fluids to flow through valve 62. This suction output 64 is configured to be in fluid communication with opening 3. In addition, a pressure sensor 66 is coupled to and in communication with micro controller 50. This pressure sensor is configured to determine how much fluid is being sucked as well as how much pressure is being applied to the suction output.

FIG. 4 shows a flow chart for one process that can be used with micro controller or microprocessor 50. This process can be in the form of a series of instructions that are stored in the memory which is part of microprocessor 50. Microprocessor 50 then accesses this memory in order to achieve these steps. For example, this process includes step S1 which includes a power on or initialization which includes turning the system on via keyboard 4. Next, the user can attach components to the pump, such as attaching a tube or suitable fluid channel to the pump such as tube 6. In step S3, microcontroller 50 starts a first phase which is a phase that includes three different settings for frequency and amplitude for pumping pressure as indicated in steps S4, S5, and S6. For example, if this pump 1 is being used as a breast pump, this first phase is designed to simulate a period of time when a baby first latches on to a woman's breast. This first phase could last for any preset period of time, but in this case, the first setting includes a first range such as 60 to 80 cycles per minute at 30% of full power of suction lasting 7 to 10 seconds. In this case, in at least one embodiment a full power setting can be in the form of 250 mmHg of pressure. The second setting in step S5 changes the percentage of suction power from an initial setting of 30% to 75% lasting 2 to 4 seconds. Then in step S6, the system will reverse back to step S4 where it is 30% of suction percentage for 7 to 10 seconds again. This pattern then repeats itself during the entire phase.

The second phase which is initiated in step S7 as indicated includes a range of 30-40 cycles per minute at 30% of full pressure or power lasting 7-10 seconds in a first setting in step S8, and then proceeds to a second setting in step S9 wherein the power or suction switches to 75% of maximum lasting 2 to 4 seconds. Then in step S10 a pause is periodically initiated. This pause creates the simulation of a child swallowing milk. This periodic pause can occur at preset intervals and can occur for a preset period of time. For example, this pause can be set between the first setting and the second setting, or this pause can be set at the end of the second setting in step S9. In step S11 the fourth setting, the process reverts back to step s8 where the system reverts back to 30% of maximum pressure for 7 to 10 seconds again. This pattern will repeat itself during the entire phase. This phase can extend for a predetermined period of time such as 1 minute, 5 minutes 10 minutes or even more than 10 minutes.

The effects of the periodic breaks in sucking create a situation wherein this pause setting (See FIG. 5) as indicated in step S10 more closely duplicates a live breastfeeding experience. One of the implications of this added technology may confer an additional benefit to the mother's breast during lactation as the natural pattern is more closely simulated. Some of the possible benefits of these breaks are:

Less stress on the milk ducts and breast tissue;
Less stress on the ligaments supporting the breast;
Enhanced milk production by mimicking more closely the natural pattern of a baby feeding.

Figure 5:
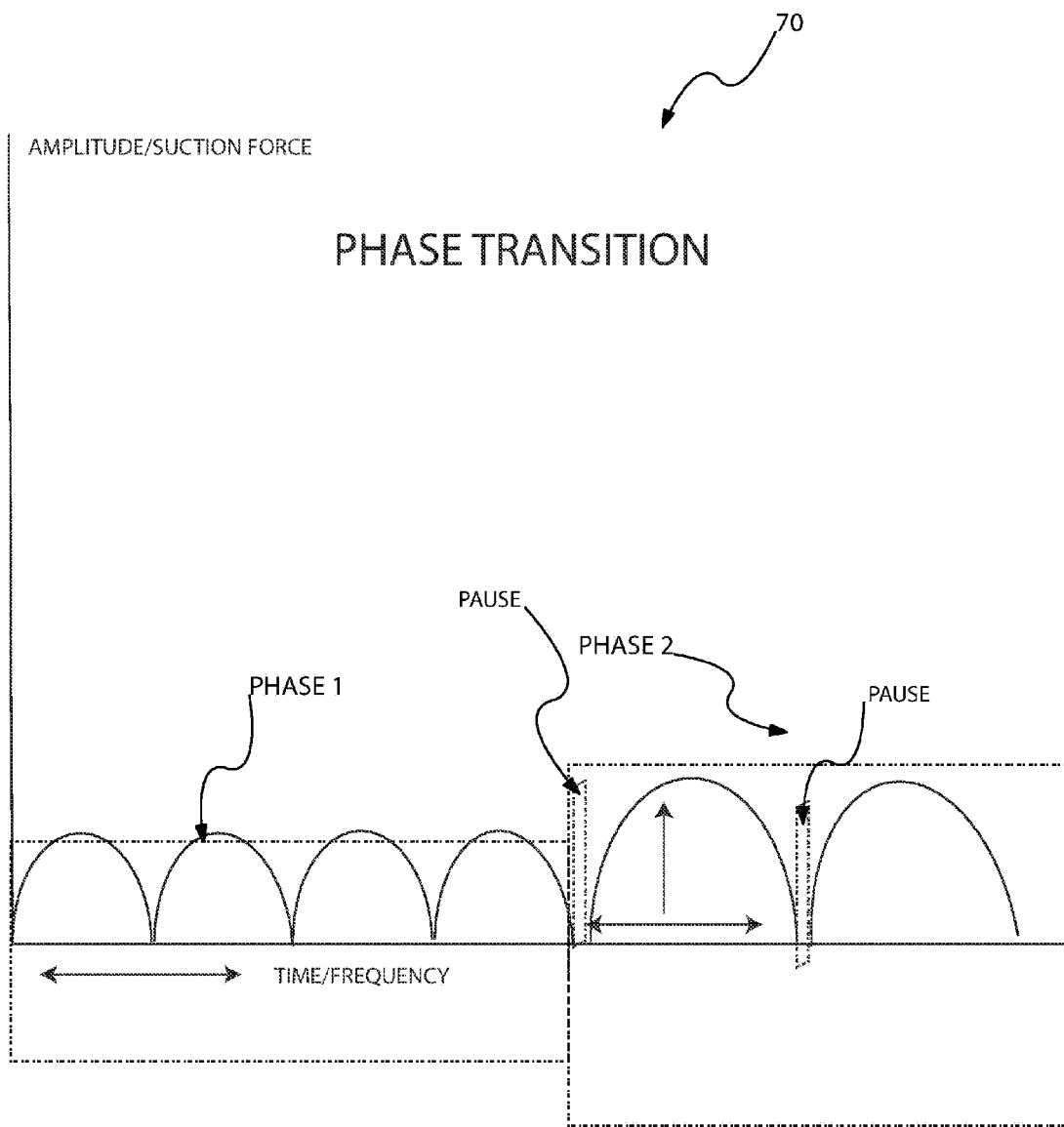
FIG. 5 is a graph of the phase transition from a first phase to a second phase for the pump.

This process is shown by way of a graph as well which as shown in FIG. 5. In this view, there is shown examples of frequency and amplitude of pressure applied and the temporary pauses that can be incurred as well.

FIG. 6 shows a flow chart for another process that can be initiated by the system as well and performed by microprocessor 50.

For example, in this process, in step S20, the user presses a menu button at a period of time before the time to initiate the breastfeeding process. At this point, the user in step S21 can create a set of preset settings such as the time for initiation of a series of breastfeeding pumping exercises. For example, this series can be for example 10 or more different ½ hour sessions for breast pumping using the two phases outlined in FIG. 3. Next, in step S23 the user can scroll via keypad 4 and screen 5 to a first set of preset settings such as to a period of time to start the initiation of a breastfeeding cycle such as a breastfeeding cycle shown in FIG. 3.

Next, in step S24 the user can press on keypad 4 to press start to initiate the program. This starts a timer or clock in step 25 wherein that time was created originally in step S21. The timer is set to either a particular day of the week or a particular time of day so that a user can then have the machine automatically pump milk.

For example, for those practicing in the orthodox faith, Shabbat is observed with severe restrictions on how a user can operate machinery or electronic devices. For example, the user may be restricted from pushing any buttons such as on an elevator or on a breast pump during the hours of Shabbat. The period of time for Shabbat is observed from a few minutes before sunset on Friday evening, until the appearance of three stars in the sky on Saturday night. Many rabbinical scholars have pointed out that these regulations of labor have something in common-they prohibit any activity that is creative, or that exercises control or dominion over one's environment. In addition, many of these activities are also prohibited on the Jewish holidays listed in the Torah, although there are significant exceptions permitting carrying and preparing food under specific circumstances.

Next in step S26, the user can select or press exit or end to leave the machine dormant until the time that it automatically initiates in step S27. In step S27, the total cycle of the first phase and the second phase can initiate for a period of time such as for 5 minutes, 10 minutes 30 minutes or 40 minutes. In at least one embodiment, this cycle for pumping breast milk for 30 minutes would be executed every three hours until Saturday 10 P.M. when the Shabbat mode or preset mode would automatically shut off.

To preserve the strict adherence to Talmud law and orthodox beliefs, the system can be set or optionally restricted so that the Shabbat events cannot be adjusted when the Shabbat mode is activated. In step S28, the array of events such as the approximately 10 breastfeeding events can be listed on display 5 during the Shabbat period of time so that the user, without pressing any buttons, can read and review the schedule for using the device 1. In step S30, the time period ends so that the device returns to its normal non preprogrammed routine for the rest of the week. This device can then be automatically reactivated by automatically returning to step S27 at the start of the next Shabbat period of time.

Thus, this system results in a breastfeeding device that can be pre-programmed to have periodic pauses and different types of sucking cycles which allow for an accurate modeling of a woman breastfeeding a child. In at least one embodiment, the device including any software which can be programmed thereon, is configured to mimic or model itself towards a suction pattern of a child on a woman who is lactating, or in the process of breastfeeding. In addition, this system and process can also result in a pre-programmable breastfeeding pump, which creates a preset time for initialization and a preset schedule of a series of events for breastfeeding over a period of time such as over a 24 hour or 30 hour period of time so that the user can automatically use the breast pump without having to use any of the keys 4 on the keyboard.

At least one embodiment of the present invention has the capability to capture, retrieve and transmit data via GPRS, WIFI, BLUETOOTH, or ANY wireless communication devices. The data capture will be sent to a remote web server, where the data will be collected and stored. All data transfer will be encrypted to ensure proper security.

Figure 7:
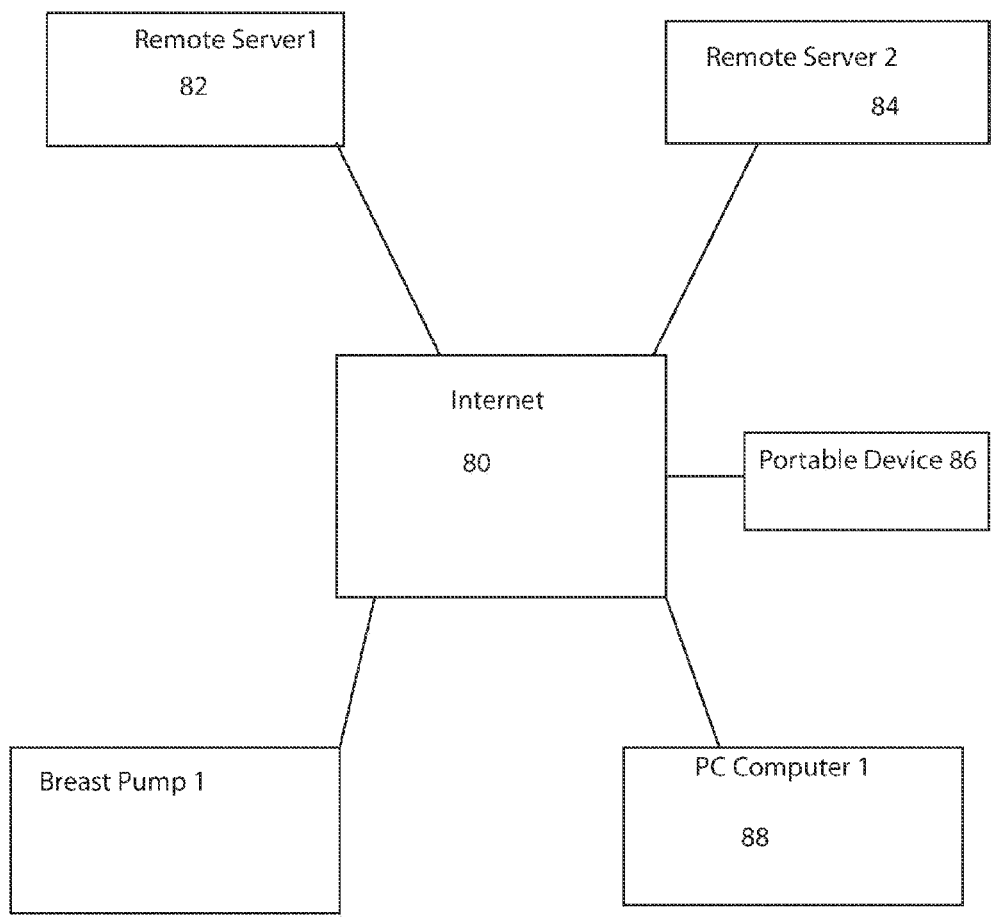
FIG. 7 is a schematic block diagram of a computer network.

As shown in FIG. 7 the system can be configured so that there is a remote server 82, a remote server 84, wherein both of these servers are connected through the internet 80 to a breast pump 1 (See FIG. 1) or to a PC computer 88. There is a portable device 1 which is coupled to the internet 80 which is configured to communicate with these two servers as well. In this embodiment, the breast pump 1 is configured to communicate through wireless communication protocols to the internet 80 so that information is sent and received into the breast pump 1 and communicated with servers 82 and 84. At least one of the servers 82 and 84 is configured to house information, and at least one of the serves 82 and 84 is configured as an application server as well.

Figure 8:
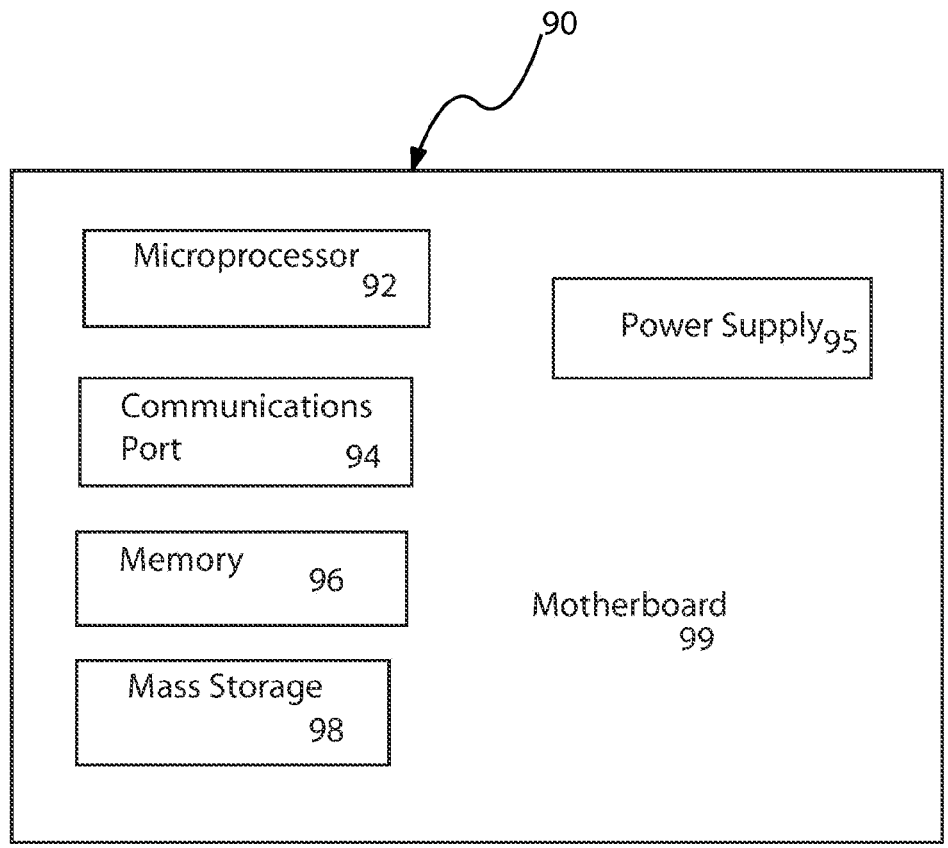
FIG. 8 is a schematic block diagram of a microprocessor for use with the components of the computer network.

FIG. 8 shows the individual components that can be housed inside of each of the different components. For example, inside of each of these components such as server 82, server 84, portable device 86 there can be the components shown in FIG. 8. For example in FIG. 8 there is shown a motherboard 99 which is coupled to microprocessor 92. There is also a communications port 94, a memory 96, a mass storage 98, and a power supply 95 all coupled to motherboard as well. These components are configured to communicate with each other so that each of the serves 82, 84, 86, and pc 88 can operate or run programs associated with breast pump 1 wherein these programs are shown in FIG. 9. With this style system, the user can pre-program the breast pump remotely using a PC (personal computer such as PC 88 a portable device such as a smartphone 86, or any other data input or computing device.

Figure 9A:
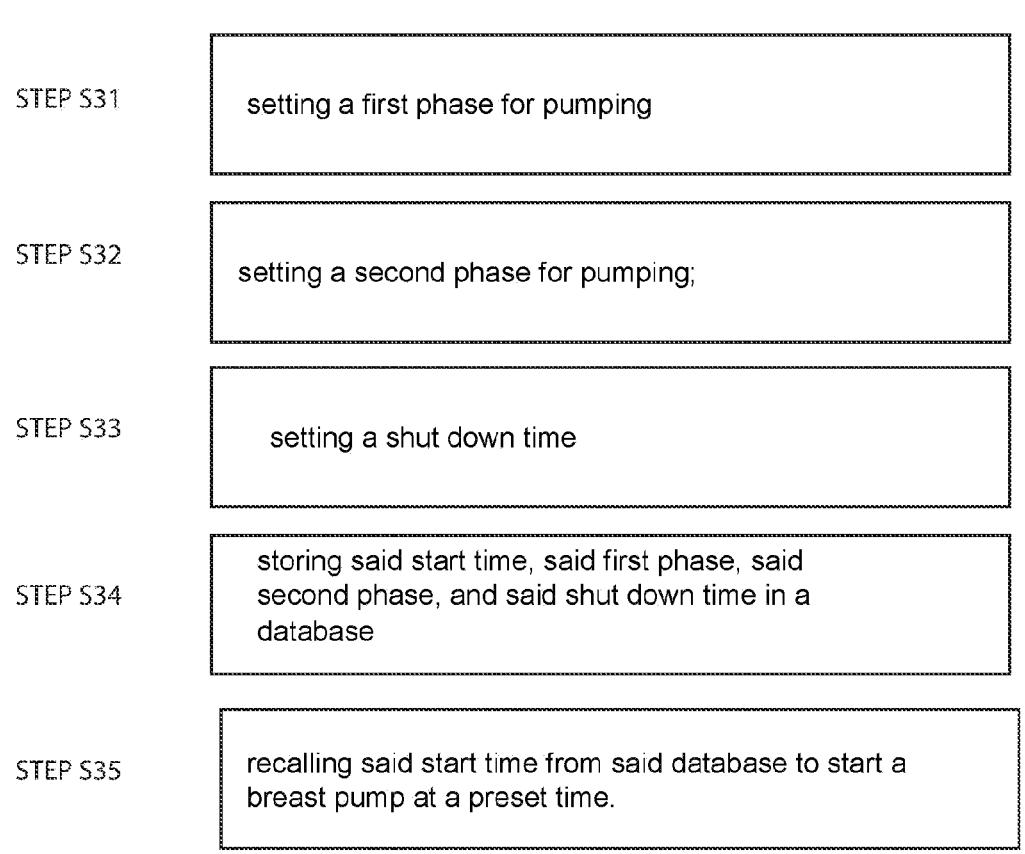
FIG. 9A is a process for programming a breast pump from a remote location.

FIG. 9A discloses the process for setting or pre-programming the device as well. For example, the process can start in step S31 wherein the user sets a start time. This start time can be recorded into the memory or mass storage such as mass storage 98 of server 82 or 84. Next, the process can include setting a first phase for pumping in step S32. This first phase can also be stored in memory 96 or mass storage 98 of server 82 or 84. Next, step S33 includes setting a shut down time, which can be set in memory 96 or mass storage 98 of server 82 or 84 as indicated for steps S31, S32, and S33 in step S34. Next, step S35 involves recalling the start time from the database to start a breast pump at a preset time. Steps S31-S33 can be performed using any one of portable device 86, PC Computer 88 or any other type of remote device.

Figure 9B:
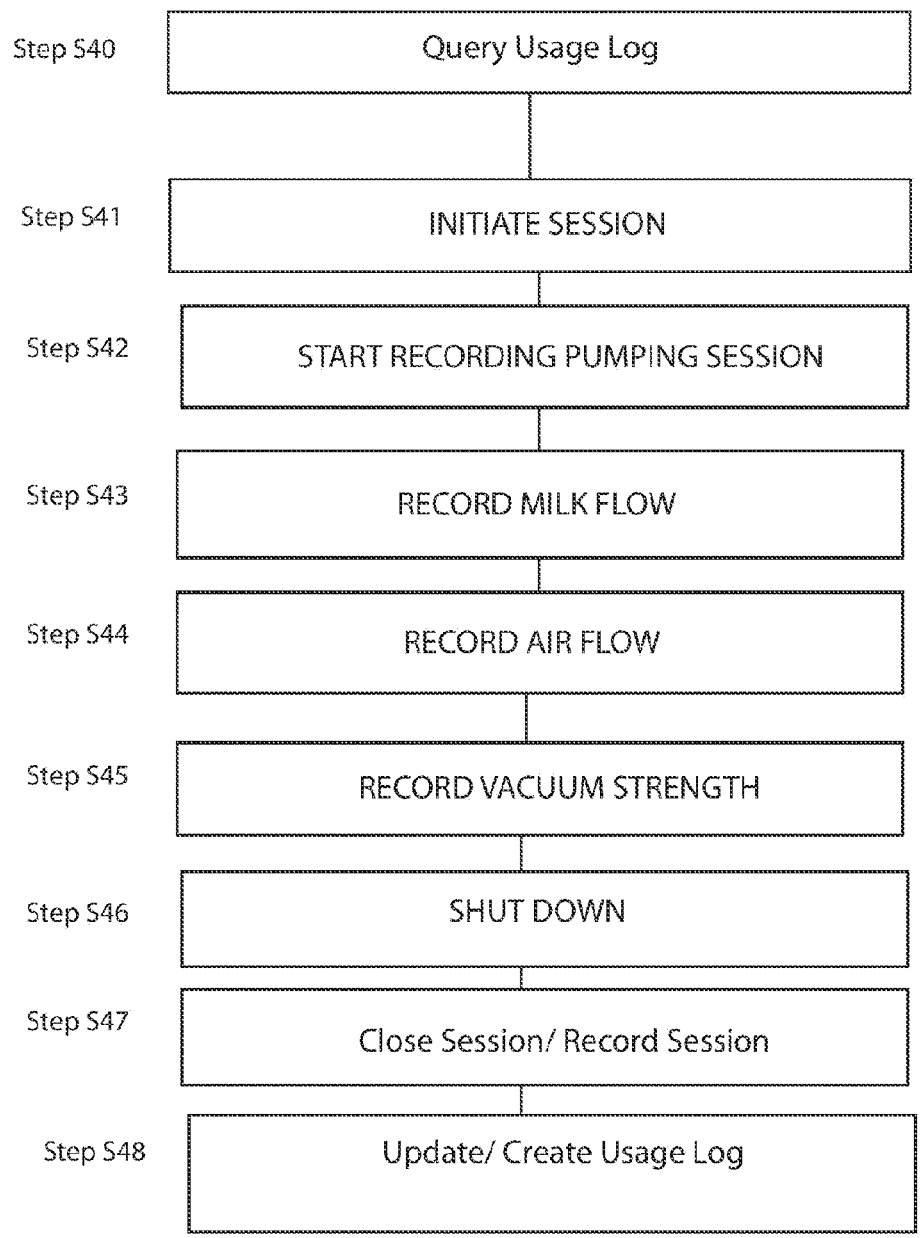
FIG. 9B is a process for tracking the usage and types of usage of the pump.
Figure 10:
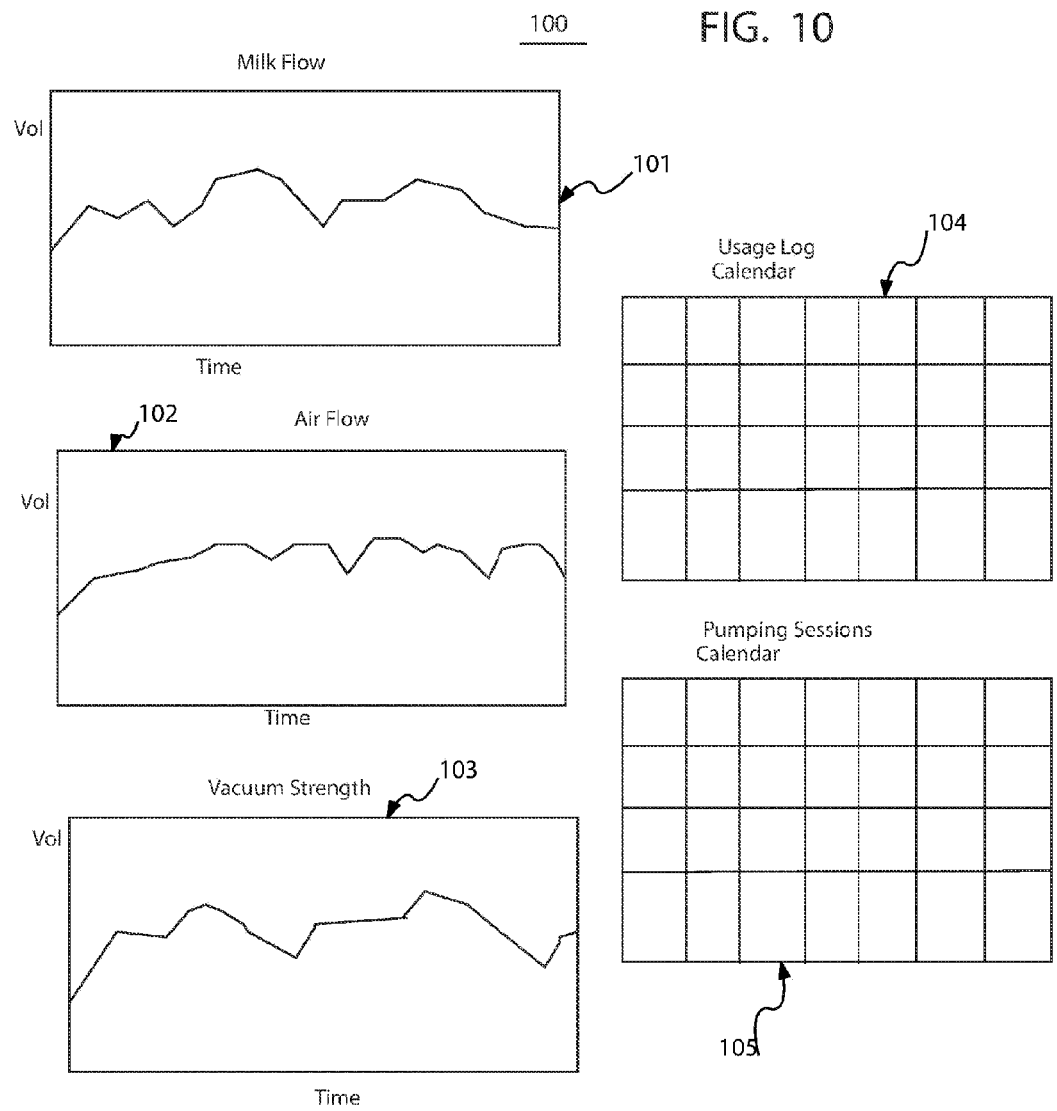
FIG. 10 is a screen shot of the reporting of the device.

The process for recording and reporting the information relating to a breast pump is shown in greater detail in FIG. 9B. For example, this process includes the breast pump periodically querying the usage log to determine whether it should turn on or off in step S40. Next, in step S41 it can initiate a session by either a user turning on a breast pump or by automatically turning on the breast pump. Next, in step S42 the system can start recording the pumping session and storing this information in a database in at least one of servers 82 and 84. Next, in step S43 the system can record the milk flow through the system as shown by way of example in FIG. 10 in graph 101 which indicates the volume of milk flow through the system at a given period of time. This fluid flow can be determined via flow meter 6.1 in line 6. This flow meter is in communication with pump 1 such that this information can then be communicated to either one of servers 82 or 84. Alternatively, the system can be used without a flow meter wherein the motor, 60, the pressure sensor 66, and the suction output 64 can be used either alone or in combination with any one of the above to determine the milk flow. Next, in step S44 the system can record the air flow through the pump 1 such that this air flow is controlled by the suction output 64 and monitored by the pump 1 directly. In particular, it can be monitored by any one of motor 60, valve 62, suction output 64, an pressure sensor 66 either alone or in combination with any of the other to determine the air flow through the pump. This information is shown via chart 102 in FIG. 10. The vacuum strength is recorded in step S45 wherein this vacuum strength is recorded via motor 60 and the readout of this motor which is fed wirelessly to servers 82 and 84. This information is shown via chart 103 in FIG. 10. Once this milk flow, air flow, and vacuum strength is determined, it can be logged into a usage log calendar 104 so that this information is then recorded. As shown in FIG. 10 there is also a pumping sessions calendar as well which is used to selectively turn on the pump and turn off the pump on a pre-scheduled basis as well.

As indicated above, the breast pump 1 is configured to relay the following information into servers 82 and 84: 1) Milk flow; 2) Air flow; 3) Pumping sessions; 4) Usage log; 5) Vacuum strength; 6) remote control information; 7) custom suction patterns.

The milk flow data can be used for several analyses. It can be used to determine the amount of milk that the mother is producing, it can determine if sufficient milk is being produced, and it can make recommendations as to how to improve milk productivity. It provides a convenience to lactation nurse who can remotely monitor and communicate efficiently to the mothers who are lactating. It can also provide immediate intervention if something goes wrong.

The air flow data is collected to ensure that the pump is pumping at a consistent rate, and that the mother or person breast feeding is getting sufficient suction based on the settings that they feel comfortable with. The air flow can be remotely controlled to provide immediate assistance if the user is not using it correctly or is feeling uncomfortable.

The pumping sessions data will be used as a daily/monthly log to track and chart their usage. It will be useful to monitor the amount of usage vs the increase/decrease in milk production, to ensure that the user's do get the maximum benefit out of using a breast pump, and that lactation nurse will also use this data log to provide proper recommendation to diagnose if there is a problem.

The usage log will be similar to the pumping sessions, and it will serve as a chart to track the usage of the mothers. The usage log can also be programmed locally and remotely to the breast pump, for religious purposes to turn on automatically and shut off automatically to enable usage towards a certain demographic of users. (Shabbat mode)

The vacuum strength data is important for the machine to ensure that the mothers are getting the appropriate suction. The system will also self-calibrate with the server if the vacuum strength is not what it is supposed to be set at. Vacuum strength can also be manually remote controlled if and when the mothers have issue with the machine and do not know what to do with it. The lactation nurse will remote control the vacuum strength.

The two-way remote control will be a two-way data communication which enables the machine to be controlled remotely, turning on/off, increasing/decreasing pressure, programming the auto/Shabbat mode. It also enables the lactation nurse to analyze data of the mother's usage to make sure she is getting the most out of using a breast pump.

In addition, there can be a customization of a suction pattern. For example, for certain mothers, the suction pattern of each child might be different. The remote control feature will enable lactation nurse or lactation technologist to program accordingly to the child's suck swallow pattern. This enables the mother to feel comfortable and ensure continuous milk flow.

Thus, this system is configured to create a breast pump that can have its activity pre-programmed so that the user does not have to push an excessive amount of buttons. In addition, the system is configured to create a breast pump that can be used to record the usage of the breast pump into a computer network so that the system can relay back to the user the information relating to the usage so that the user can view the quality of the breast pumping session.

Accordingly, while at least one embodiment of the present invention have been shown and described, it is to be understood that many changes and modifications may be made thereunto without departing from the spirit and scope of the invention as defined in the appended claims.

What is claimed is:

1. A process for controlling and recording the actions of a breast pump comprising the following steps:
   querying a usage log to determine whether a pumping session has been scheduled;
   initiating a pumping session when a usage log determines that it is time to start pumping;
   setting a first phase for pumping comprising a first amplitude designating suction force wherein said first phase does not include pauses in suction cycling;
   setting a second phase for pumping comprising a second amplitude designating suction force, wherein said second phase has intermittent pauses;
   recording an amount of milk flowing due to the breast pump pumping;
   storing information relating to the amount of milk flowing in a server, by storing the information across at least a month to provide a monthly log to track usage; and
   reporting on the amount of milk flowing due to the breast pump pumping by providing a chart across at least a month to track each usage.

2. The process as in claim 1, further comprising the step of: recording an amount of air flow in the system due to the breast pump pumping and then tracking and charting the amount of air flow to provide a monthly log to track air flow of the breast pump.

3. The process as in claim 2, further comprising the step of recording a vacuum strength of the breast pump pumping and then tracking and charting the amount of vacuum strength in the breast pump to provide a monthly log to track vacuum strength of the breast pump.

4. The process as in claim 1, further comprising the following steps:
   setting a start time;
   setting a shut down time;
   storing said start time, said first phase, said second phase, and said shut down time in a database; and
   recalling said start time from said database to start a breast pump at a preset time.

5. The process as in claim 1, wherein said first phase has a first setting of amplitude and frequency for pumping, and wherein said second phase has a second setting of amplitude and frequency for pumping.

6. The process as in claim 1, further comprising the step of recording a usage log for the pump.

7. The process as in claim 1, further comprising the step of recording and scheduling a pumping session.

8. The process as in claim 1, wherein said scheduled pumping session is configured to start pumping automatically once the scheduled pumping session starts.

* * * * *